US005785867A

United States Patent [19]

LaZonby et al.

[11] Patent Number: 5,785,867
[45] Date of Patent: Jul. 28, 1998

[54] METHOD AND COMPOSITION FOR INHIBITING GROWTH OF MICROORGANISMS INCLUDING PERACETIC ACID AND A NON-OXIDIZING BIOCIDE

[75] Inventors: Judy G. LaZonby, Crystal Lake; Robert E. McCarthy, Naperville; Nancy L. Casselman, Wheaton, all of Ill.

[73] Assignee: Nalco Chemical Company, Naperville, Ill.

[21] Appl. No.: 848,326

[22] Filed: Apr. 30, 1997

Related U.S. Application Data

[63] Continuation-in-part of Ser. No. 559,685, Nov. 15, 1995, Pat. No. 5,658,467, which is a continuation-in-part of Ser. No. 350,570, Dec. 7, 1994, Pat. No. 5,494,588, which is a continuation-in-part of Ser. No. 102,286, Aug. 5, 1993, abandoned.

[51] Int. Cl.⁶ .................................. C02F 1/50; C02F 1/72
[52] U.S. Cl. ......................... 210/759; 210/764; 514/439; 514/557; 514/714; 252/175; 252/180
[58] Field of Search ........................... 210/764, 754, 210/755, 759; 514/557, 714, 439; 252/175, 180, 181

[56] References Cited

U.S. PATENT DOCUMENTS

| 5,200,189 | 4/1993 | Oakes et al. ........................... 424/405 |
| 5,494,588 | 2/1996 | LaZonby ................................. 210/764 |

*Primary Examiner*—Neil McCarthy
*Attorney, Agent, or Firm*—Kelly L. Cummings; Thomas M. Breininger

[57] ABSTRACT

The present invention provides a composition and method of administering same for inhibiting the growth of microorganisms. The composition of the present invention includes sufficient amounts of a peracetic acid or peracetic acid/peracid blend and a non-oxidizing biocide. The method of the present invention includes the step of adding sufficient amounts of the peracetic acid or peracetic acid/peracid blend and the non-oxidizing biocide to industrial process waters.

9 Claims, No Drawings

METHOD AND COMPOSITION FOR INHIBITING GROWTH OF MICROORGANISMS INCLUDING PERACETIC ACID AND A NON-OXIDIZING BIOCIDE

BACKGROUND OF THE INVENTION

1. Reference to Related Patent

The present application is a continuation-in-part of application Ser. No. 08/559,685, filed Nov. 15, 1995, by Judy G. LaZonby, Robert E. McCarthy and Nancy L. Casselman, entitled "Method and Composition For Inhibiting Growth of Microorganisms Including Peracetic Acid and a Non-Oxidizing Biocide", now U.S. Pat. No. 5,658,467, which is in turn a continuation-in-part of application Ser. No. 08/350,570, filed Dec. 7, 1994, now U.S. Pat. No. 5,494,588 and issued Feb. 27, 1996 to Judy G. LaZonby, entitled "Method and Composition For Inhibiting Growth of Microorganisms Including Peracetic Acid and a Non-Oxidizing Biocide", which is a continuation-in-part of application Ser. No. 08/102,286, filed Aug. 5, 1993, by Judy G. LaZonby, entitled "Method and Composition for Inhibiting Growth of Microorganisms Including Peracetic Acid and a Non-Oxidizing Biocide", now abandoned, the disclosures of which are incorporated herein by reference.

2. Field of the Invention

The present invention relates generally to controlling the growth of microorganisms. More specifically, the present invention relates to inhibiting the growth of microorganisms in industrial waters.

3. Background of the Invention

The presence of microorganisms in waters, especially industrial waters, is a never-ending concern for industrial manufacturers. Examples of industrial waters where microorganisms can interfere with industrial processes include: cooling tower waters; mining process waters; food processing waters; papermaking slurries; pulp and paper mill waters; sugar reprocessing waters; and the like.

In the paper industry, the growth of microorganisms in pulp and paper mill waters can adversely affect finished paper products. Microbial life depends on nutrients, pH and temperature of a particular system. The warm temperatures and rich carbohydrate containing fluids of paper machines and process streams provide ideal growth conditions for a variety of microorganisms. These contaminating microorganisms are capable of causing spoilage of pulp, furnish, or chemical additives. The microorganisms cause deposits that break loose and fall into the paper furnish, resulting in quality loss and/or end product defects such as holes and spots. The end result is unsalable paper or paper sold at a lower value. Robertson, *The Use of Phase-Contrast Microscopy to Assess and Differentiate the Microbial Population of a Paper Mill*, TAPPI Journal, pp. 83 (March 1993).

The presence of microorganisms within industrial water systems results in the formation of deposits of biological origin on industrial machines. These deposits give rise to: corrosion; breaks; increased down time; loss of yield; high chemical costs; odors; and expensive deposit control programs. In the paper mill industry, slime deposits are reportedly responsible for nearly 70% of all breaks, blockages and pump failures. Safade, *Tackling the Slime Problem in a Paper Mill*, PTI, p. 280 (September 1988).

Slime may be defined as an "accretion or accumulation caused by certain microorganisms in the presence of pulp fiber, filler, dirt and other materials, mixed in varied proportions, having variable physical characteristics and accumulating at continuously changing rates." Id. In most industrial process waters, especially pulp and paper mill systems, spore forming bacteria and *Pseudomonas aeruginosa* contribute to slime formation. The later is most prevalent in paper mill slimes. Fungi is also a contributor of slime formation.

The conventional method of controlling microbial growth is through the use of biocides. Biocides are generally divided into two main groups: oxidizing; and non-oxidizing. These biocides act on the microorganisms in one of three ways: either by attacking the cell wall; the cytoplasmic membrane; or the cellular constituents. Id. at 282.

While biocides do inhibit microbial growth, economic and environmental concerns require improved methods. A problem with the use of biocides is that high levels of expensive chemicals are needed to control microbial growth. To date, none of the commercially available biocides have exhibited a prolonged biocidal effect. Their effectiveness is rapidly reduced as a result of exposure to physical conditions such as temperature or association with ingredients contained by the system toward which they exhibit an affinity. This results in a restriction or elimination of their biocidal effectiveness.

Therefore, the use of such biocides involves continuous or frequent additions to paper mill systems. Further, these additions must be made at a plurality of points or zones in the system. The costs of the biocides and the labor costs involved are considerable.

Moreover, such chemicals are highly toxic in the quantities known to be required for effective control of microbial populations. As a result, environmental regulations restrict the amount of biocides that can safely be discarded into the environment. Therefore, a need exists for improved methods for controlling the growth of microorganisms in industrial process waters.

Peroxy-containing compositions are known for use in the production of microbicidal agents. One such composition is disclosed in Bowing et al., U.S. Pat. No. 4,051,059 containing peracetic acid, acetic acid or mixtures of peracetic and acetic acid, hydrogen peroxide, anionic surface active compounds such as sulfonates and sulfates, and water.

Peracetic acid has been shown to be a good biocide, but only at fairly high concentrations (generally greater than 100 part per million (ppm)). Similarly, peroxyfatty acids have also been shown to be biocidal, but only at high concentrations (greater than 200 ppm), such as in the composition disclosed in European Patent Application No. 233,731.

Peracetic acids have been shown to exhibit synergy in combination with a number of biocides as shown in U.S. Pat. No. 5,494,588, the disclosure of which is incorporated herein by reference. U.S. Pat. Nos. 5,200,189 and 5,314,687, issued to Oakes, et al., the disclosures of which are incorporated herein by reference, discuss the use of antimicrobial compositions comprising a diluted combination of a $C_1$ to $C_4$ peroxycarboxylic acid and a $C_6$ to $C_{18}$ peroxyacid.

SUMMARY OF THE INVENTION

Pursuant to the present invention, the growth of microorganisms can be inhibited without the use of high levels of certain organic peroxide biocides such as peracetic acid and other peracids. The present invention provides compositions to be used for controlling the growth of microorganisms in industrial process waters. The compositions may include sufficient amounts of a peracetic acid and a non-oxidizing biocide or a blend of peracetic acid and other peracids used in combination with a non-oxidizing biocide.

The present invention also provides a method for inhibiting the growth of the microorganisms in industrial process waters. Preferably, these process waters may be selected from the group consisting of pulp and paper mill process waters, industrial cooling waters and mining waters. The method includes the step of adding to the waters sufficient amounts of a peracetic acid (PAA) or a peracetic acid/peracid blend and a non-oxidizing biocide. Combining the peracetic acid or peracetic acid/peracid blend with the non-oxidizing biocide has been found to enhance the effectiveness of the non-oxidizing biocide.

DETAILED DESCRIPTION OF THE PREFERRED EMBODIMENTS

The present invention provides, under one embodiment for inhibiting the growth of microorganisms, improved organic peroxide compositions and method of administering the same to a fluid system. The compositions include a sufficient amount of a peracetic acid or other organic peroxide and a non-oxidizing biocide.

The biocide component of this invention includes biocides that exhibit a synergistic effect when added to a fluid stream with a peracetic acid. Examples of suitable non-oxidizing biocides include 2-methyl-4,5-trimethylene-4-isothiazolin-3-one and 2-(thiocyanomethylthio) benzothiazole. Mixtures of such biocides are also contemplated within the claims of the invention.

The biocides of the invention can be obtained from a number of chemical suppliers such as American Cyanamid, Buckman, Betz, Dearborn Chemical, Economics Laboratory, Inc., Merck, Nalco Chemical Company, and Vineland Chemical.

Peracetic acid may also be obtained from a number of chemical suppliers. One such supplier is FMC Corporation of Philadelphia, Penna.

The combination of a peracetic acid along with such non-oxidizing biocides provides an unexpected synergistic relationship. The synergistic relationship is present in that the cooperative action of the combined peracetic acid with the non-oxidizing biocides yields a total effect which is greater than the sum of the effects of the biocide or the peracetic acid taken separately.

The optimal amounts of biocide and peracetic acid required for effectiveness in this invention depend on the type of industrial waters being treated. In addition, the concentration of the combined components varies greatly and can depend upon the conditions such as temperature and pH of the waters, and the microbial count. The concentrations may be as little as 1 part per million (ppm) by weight to as much as 250 ppm. With respect to the biocide, the lower and upper limits of the required concentration substantially depend upon the specific biocide or combination of biocides used.

Still further, since the suitable biocides that may be used in the present invention are often obtained at different usable concentrations (i.e. activity level), the ratios vary depending on the particular biocide combined with the peracetic acid. For example, the peracetic acid used in the examples below is 5% active, the glutaraldehyde is 50% active, and the DBNPA is 20% active. Thus, a 1:1 ratio of PAA:Glut translates to 1:10 on an actives basis, while a 1:1 ratio of PAA:DBNPA translates to a 1:4 based on actives.

By way of example, and not limitation, the following are biocides, including the percent active of each biocide, that may be used in the present invention 2-methyl-4,5-trimethylene-4-isothiazolin-3-one (5% a.i.) and 2-(thiocyanomethylthio)benzothiazole (30% a.i.), wherein "a.i." represents active ingredient.

Pursuant to the method of the present invention, the growth of microorganisms in industrial process waters can be inhibited. The method comprises the step of adding to the waters the peracetic acid and the nonoxidizing biocide of the present invention. In one embodiment, the biocide and the peracetic acid are separate components that are added to the system.

In a preferred embodiment, the peracetic acid is added to the industrial water prior to the addition of the non-oxidizing biocide. The peracetic acid can be added pursuant to any known method that provides the desired concentration of the same in the waters.

After the controlled addition of the peracetic acid, the non-oxidizing biocide is then added to the water system. In an embodiment, the non-oxidizing biocide is added 30 minutes after the peracetic acid is added to the system. Similar to the peracetic acid addition, the biocide can be added pursuant to any known method that provides the desired concentration of the biocide in the waters.

In an embodiment, the method comprises adding approximately 5 to 250 ppm of the non-oxidizing biocide along with approximately 10 to 250 ppm of the peracetic acid. In an embodiment, the biocide and the peracetic acid are present in a range from about 1 ppm to 1000 ppm of product.

Peracetic acid is a unique oxidant, utilizing a different mode of action than other oxidants. Given the structure of the molecule:

the hydrocarbon tail allows PAA to penetrate into the bacterial cell. This enables the molecule to disrupt S—S and S—H bonds both inside and outside of the organisms, killing more quickly and effectively than other oxidants. Other oxidants, such as $HOCl$, $ClO_2$, $H_2O_2$, etc. do not penetrate the cells in this manner because they do not have an organic portion to facilitate entrance into the bacterial cell.

Peracetic acid has always been applied by itself in high concentrations. Because it is also an equilibrium molecule, in that it dissociates back to its starting product after it is diluted, it was never expected to be active at low concentrations. However, its dissociation rate is much slower than expected, giving an unexpected synergy with other biocides when it is applied at low concentrations (as low as 10 ppm of a 5% product or 0.5 ppm active).

Peracetic acid has been used as a sterilant in the food industry for many years, but is generally used at higher concentrations (10,000 to 100,000 ppm). Until recently it has not been used in the paper industry for the control of microorganisms in the papermachine process water.

Peracetic acid is made up of a blend of hydrogen peroxide and acetic acid. When longer chained carboxylic acids are used in place of acetic acid, other peracids are formed, some of which exhibit antimicrobial activity against bacteria and fungi. These alternate peracid blends demonstrate the same synergistic activity with non-oxidizing biocides as does peracetic acid since their mode of action is the same.

A variety of $C_6$—$C_{18}$ peroxyacids may be employed in the composition of the invention, including peroxyfatty acids, monoperoxy- or diperoxydicarboxylic acids, and peroxyaromatic acids. The $C_6$—$C_8$ peroxyacids employed in the present invention may be structurally represented as follows: $R_1$—$CO_3H$, wherein $R_1$ is a hydrocarbon moiety having from about 5 to 17 carbon atoms (a $C_{18}$ peroxyacid is generally represented structurally as $C_7$—$CO_3H$). $R_1$ may have substituents in the chain, e.g., —OH, $CO_2H$, or heteroatoms (e.g., —O— as in alkylether carboxylic acids). $R_1$ may be linear, branched, cyclic or aromatic. Preferred hydrocarbon moieties (i.e. preferred $R_1$'s) include linear, saturated, hydrocarbon aliphatic moieties having from 7 to 11 carbon atoms.

Specific examples of suitable $C_6$—$C_{18}$ carboxylic fatty acids which can be reacted with hydrogen peroxide to form peroxyfatty acids include such saturated fatty acids as hexanoic ($C_6$), enanthic (heptanoic) ($C_7$), caprylic (octanoic) ($C_8$), pelargonic (nonanoic) ($C_9$), capric (decanoic) ($C_{10}$), undecyclic (undecanoic) ($C_{11}$), lauric (dodecanoic) ($C_{12}$), trideclic (tridecanoic) ($C_{13}$), myristic (tetradecanoic) ($C_{14}$), palmitic (hexadecanoic) ($C_{16}$), and stearic (octodecanoic) ($C_{18}$). These acids can be derived from both natural and synthetic sources. Nastural sources include animal and vegetable fats or oils which should be fully hydrogenated. Synthetic acids can be produced by the oxidation of petroleum wax. Particularly preferred peroxyfaty acids for use in the composition of the invention are linear monoperoxy aliphatic fatty acids such as peroxyoctanoic acid, peroxydecanoic acid, or mixtures thereof.

Other suitable $C_6$—$C_{18}$ peroxyacids are derived from the oxidation of dicarboxylic acids and aromatic acids. Suitable dicarboxylic acids include adipic acid ($C_6$) and sebacic acid ($C_{10}$). An example of a suitable aromatic acid is benzoic acid. These acids can be reacted with hydrogen peroxide to form the peracid form suitable for use in the composition of the invention. Preferred peracids in this group include monoperoxy- or diperoxyadipic acid, monoperoxy- or diperoxysebacic acid, and peroxybenzoic acid.

The above peroxyacids provide antibacterial activity against a wide variety of microorganisms, such as gram positive (e.g., *Staphylococcus aureus*) and gram negative (e.g., *Escherichia coli*) microorganisms, yeast, molds, baterial spores, etc.

The antimicrobial composition of the present invention can comprise about 0.01 to 10 wt. %, preferably about 0.05 to 5 wt. %, and most preferably about 0.1 to 2 wt. % of a $C6$—$C_{18}$ peroxyacid, and about 0.1 to 25 wt. %, preferably about 0.5 to 20 wt. %, and most preferably about 1 to 15 wt. % of peracetic acid. The composition preferably has a weight ratio of peracetic acid to $C_6$—$C_{18}$ peroxyacid of about 15:1 to 3:1. The composition of about 2 to 8, preferably about 3 to 7.

The peracid components used in the composition of the invention can be produced in a simple manner by mixing a hydrogen peroxide ($H_2O_2$) solution with the desired amount of acid. With the higher molecular weight fatty acids, a hydrotrope coupler may be required to help solubilize the fatty acid. The $H_2O_2$ solution is then added to peracetic acid to produce the peracetic acid/peracid composition of the invention. The composition can contain about 1 to 50 wt. %, preferably abut 5 to 25 wt. % of hydrogen peroxide.

The combination of a peracetic acid/peracid blend along with a non-oxidizing biocides provides an unexpected synergistic relationship. The synergistic relationship is demonstrated in that the cooperative action of the combined peracetic acid/peracid blend with the non-oxidizing biocides yields a total effect which is greater than the sum of the effects of the biocide or the peracetic acid/peracid blend taken separately.

The optimal amounts of biocide and peracetic acid required for effectiveness in the invention depend on the type of industrial waters being treated. In addition, the concentration of the combined components varies greatly and can depend upon the conditions such as temperature and pH of the waters, and the microbial count. The concentration of the peracetic acid/peracid blend may be as little as 1 part per million (ppm) by weight to as much as 250 ppm. With respect to the biocide, the lower and upper limits of the required concentration substantially depend upon the specific biocide or combination of biocides used.

Still further, since the suitable biocides that may be used in the present invention are often obtained at different usable concentrations (i.e. activity level), the ratios vary depending on the particular biocide combined with the peracetic acid/peracid blend.

The following are biocides, including the percent active of each biocide, may be used in the present invention in combination with the peracetic acid/peracid blend: isothiazolin (1.5% a.i.); glutaraldehyde (50% a.i.); methylene bisthiocyanate (10% a.i.); DBNPA (20% a.i.); carbamate (30% a.i.); quaternary ammonium compounds (31% a.i.); 4,5-dichloro-1,2-dithio-3-one (5% a.i.); 4,5-dichloro-2-N-octyl-4-isothiazolin-3-one (2% a.i.); decylthioethylamine (15% a.i.); orthophthaldehyde (20% a.i.); 2-bromo-2-nitropropane-1,3-diol (10% a.i.); 4,5-dichloro-1,2-dithiol-3-one (5% a.i.); dodecylguanidine hydrochloride (35% a.i.); 1-(3-chloroallyl)-3,5,7-triaza-1-azoniaadamantane chloride (67.5% a.i.); dibromo dicyanobutane (25% a.i.); bis (trichloromethyl)sulfone (35% a.i.); 2-methyl-4,5-trimethylene-4-isothiazolin-3-one (5% a.i.) and 2-(thiocyanomethylthio)benzothiazole (30% a.i.), wherein "a.i." represents active ingredient.

Pursuant to the method of the present invention, the growth of microorganisms in industrial process waters can be inhibited. The method comprises the step of adding to the waters the peracetic acid/peracid blend and the nonoxidizing biocide of the present invention. In an embodiment, the biocide and the peracetic acid/peracid blend are separate components that are added to the system.

In a preferred embodiment, the peracetic acid/peracid blend is added to the industrial water prior to the addition of the non-oxidizing biocide. The peracetic acid/peracid blend can be added pursuant to any known method that provides the desired concentration of the same in the waters.

After the controlled addition of the peracetic acid/peracid blend, the non-oxidizing biocide is then added to the water system. In an embodiment, the non-oxidizing biocide is added 30 minutes after the peracetic acid/peracid blend is added to the system. Similar to the peracetic acid/peracid blend addition, the biocide can be added pursuant to any known method that provides the desired concentration of the biocide in the waters.

The composition of the invention can be made by combining by simple mixing an effective amount of a $C_6$—$C_{18}$ peroxyacid such as a peroxyfatty acid with peracetic acid. This composition would be formulated with preformed perfatty acid and preformed peracetic acid. A preferred composition of the invention can be made by mixing peracetic acid, a $C_6$—$C_{18}$ carboxylic acid, a coupler and a stabilizer and reacting this mixture with hydrogen peroxide. A stable equilibrium mixture is produced containing a peracetic acid and a $C_6$—$C_{18}$ peroxyacid by allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, peracetic acid, a $C_6$—$C_{18}$ peroxyacid, water, and various couplers and stabilizers.

The present invention contemplates a peracetic acid/peracid composition which is diluted to a use solution prior to its utilization with the biocide of the invention.

The level of active components in the concentrate composition is dependent upon the intended dilution factor and desired acidity in the use solution. The $C_6$—$C_{18}$ peroxyacid component is generally obtained by reacting a $C_6$—$C_{18}$ carboxylic acid with hydrogen peroxide in the presence of peracetic acid. The resulting concentrate is diluted with water to provide the use solution. Generally, a dilution of 1 fluid oz. to 4 gallons (i.e. dilution of 1 to 500 by volume) or to 8 gallons (i.e. dilution of 1 to 1,000 by volume) of water can be obtained with 2% to 20% total peracids in the concentrate. Higher use dilution can be employed if elevated use temperature (greater than 20° C.) or extended exposure time (greater than 30 seconds) are also employed.

In one embodiment, the biocide and the peracetic acid/peracid blend are present in a range from about 1 ppm to 1000 ppm, respectively. In a preferred embodiment, the method comprises adding approximately 5 to 250 ppm of the non-oxidizing biocide along with approximately 10 to 250 ppm of the peracetic acid/peracid blend.

An advantage of the present invention is that it lowers the level of expensive chemicals needed for inhibiting the growth of microorganisms. With the addition of a peracetic acid in the water system, the non-oxidizing biocide is effective in low dosages, and as a result is long lasting as evidenced by reductions in microbial grow back. The increased effectiveness removes the need for repetitive additions of the biocide at multiple points in the paper making system.

A further advantage of the present invention is that it provides a more cost effective and environmentally friendly method for treating microorganisms.

By way of example, and not limitation, examples of the invention will now be given.

EXAMPLES

The following examples illustrate the synergistic relationship obtained with the compositions of the present invention.

Synergy is mathematically demonstrated by the industry accepted method described by S. C. Kull et al. in *Allied Microbiology*, vol. 9, pages 538–541 (1961). As applied to this invention, it is as follows:

$Q_A$=the ppm of active peracetic acid alone which produces an endpoint.

$Q_B$=the ppm of active non-oxidizing biocide alone which produces an endpoint.

$Q_a$=the ppm of active peracetic acid, in combination with non-oxidizing biocide, which produces an endpoint.

$Q_b$=the ppm of active non-oxidizing biocide, in combination, which produces an endpoint.

$Q_a/Q_A+Q_b/Q_B$=Synergy Index

Synergy index is

<1, it indicates synergy

=1, it indicates additivity

>1, it indicates antagonism

The following test procedures were utilized during the experimentation of the present invention.

Process water from several paper mills was obtained for test purposes. Aliquots of water from each mill were dosed with the indicated concentrations of peracetic acid (5% active obtained from FMC) or peracetic acid/peracid blend (4.5% a.i. obtained from ECO lab). After 30 minutes of contact time, the designated concentrations of non-oxidizing biocide were added to the aliquots previously dosed with PAA, mixed well and incubated at 37° C. in an orbital shaker. At the designated contact times, each aliquot was sampled to determine the total number of viable organisms in colony forming units per milliliter (CFU/mL) on Tryptone Glucose Extract (TGE) agar. An endpoint of 2, 3, 4 or 5 $\log_{10}$ reduction in viable organisms was then selected for calculating synergy.

EXAMPLE 1

Synergistic activity of peracetic acid and 2-methyl-4,5-trimethylene-4-isothiazolin-3 -one (MTI), also known as Promexal, against microorganisms in a papermill process water, pH 7.2 is shown in the following data.

| Biocide (ppm of product) | 4 Hour Contact | 24 Hour Contact |
|---|---|---|
| PAA @ 12.5 ppm | $1.5 \times 10^7$ CFU/mL | $1.5 \times 10^7$ CFU/mL |
| PAA @ 25 ppm | $1.5 \times 10^6$ CFU/mL | $1.5 \times 10^7$ CFU/mL |
| PAA @ 50 ppm | $<10^3$ CFU/mL | $2.5 \times 10^6$ CFU/mL |
| PAA @ 100 ppm | $<10^3$ CFU/mL | $<10^3$ CFU/mL |
| MTI @ 12.5 ppm | $1.6 \times 10^7$ CFU/mL | $2.2 \times 10^7$ CFU/mL |
| MTI @ 25 ppm | $1.4 \times 10^7$ CFU/mL | $1.2 \times 10^7$ CFU/mL |
| MTI @ 50 ppm | $8.0 \times 10^6$ CFU/mL | $8.6 \times 10^6$ CFU/mL |
| MTI @ 100 ppm | $6.6 \times 10^6$ CFU/mL | $4.4 \times 10^6$ CFU/mL |
| PAA @ 10 ppm plus MTI @ 12.5 ppm | $7.2 \times 10^6$ CFU/mL | $1.3 \times 10^7$ CFU/mL |
| MTI @ 25 ppm | $5.0 \times 10^6$ CFU/mL | $4.0 \times 10^6$ CFU/mL |
| MTI @ 50 ppm | $6.6 \times 10^6$ CFU/mL | $3.4 \times 10^6$ CFU/mL |
| MTI @ 100 ppm | $3.5 \times 10^6$ CFU/mL | $1.5 \times 10^6$ CFU/mL |
| PAA @ 20 ppm plus MTI @ 12.5 ppm | $1.6 \times 10^6$ CFU/mL | $6.3 \times 10^6$ CFU/mL |
| MTI @ 25 ppm | $8.5 \times 10^5$ CFU/mL | $2.7 \times 10^6$ CFU/mL |
| MTI @ 50 ppm | $7.1 \times 10^5$ CFU/mL | $2.6 \times 10^6$ CFU/mL |
| MTI @ 100 ppm | $9.0 \times 10^5$ CFU/mL | $9.0 \times 10^5$ CFU/mL |
| PAA @ 40 ppm plus MTI @ 12.5 ppm | $<10^3$ CFU/mL | $1.5 \times 10^4$ CFU/mL |
| MTI @ 25 ppm | $<10^3$ CFU/mL | $9.0 \times 10^4$ CFU/mL |
| MTI @ 50 ppm | $<10^3$ CFU/mL | $3.0 \times 10^3$ CFU/mL |
| MTI @ 100 ppm | $<10^3$ CFU/mL | $<10^3$ CFU/mL |
| Control | $2.1 \times 10^8$ CFU/mL | $1.1 \times 10^7$ CFU/mL |

Synergy Calculation:
After 24 hours of contact, a 3 $\log_{10}$ or greater reduction was achieved with:
PAA = 100 ppm
MTI = >100 ppm (200 ppm)
PAA = 40 ppm/MTI = 25 ppm
SI = 40/100 + 12.5/200 = 0.4625

EXAMPLE 2

Synergistic activity of peracetic acid and 2-(thiocyanomethylthio)benzothiazole (TCMTB) against microorganisms in a papermill process water, pH 6.6 is shown in the following data.

| Biocide (ppm of product) | 4 Hour Contact | 24 Hour Contact |
|---|---|---|
| PAA @ 50 ppm | $1.6 \times 10^8$ CFU/mL | $9.2 \times 10^7$ CFU/mL |
| PAA @ 100 ppm | $1.1 \times 10^7$ CFU/mL | $6.4 \times 10^7$ CFU/mL |
| PAA @ 200 ppm | $1.1 \times 10^7$ CFU/mL | $5.9 \times 10^7$ CFU/mL |
| TCMTB @ 50 ppm | $1.1 \times 10^8$ CFU/mL | $7.8 \times 10^7$ CFU/mL |
| TCMTB @ 100 ppm | $6.8 \times 10^7$ CFU/mL | $6.4 \times 10^7$ CFU/mL |
| TCMTB @ 200 ppm | $6.4 \times 10^7$ CFU/mL | $9.7 \times 10^6$ CFU/mL |
| TCMTB @ 400 ppm | $5.1 \times 10^7$ CFU/mL | $3.8 \times 10^6$ CFU/mL |
| PAA @ 80 ppm plus TCMTB @ 50 ppm | $1.6 \times 10^7$ CFU/mL | $4.6 \times 10^7$ CFU/mL |
| TCMTB @ 100 ppm | $9.7 \times 10^6$ CFU/mL | $3.9 \times 10^6$ CFU/mL |
| TCMTB @ 200 ppm | $5.3 \times 10^6$ CFU/mL | $1.6 \times 10^5$ CFU/mL |

-continued

| Biocide (ppm of product) | 4 Hour Contact | 24 Hour Contact |
|---|---|---|
| TCMTB @ 400 ppm | $3.6 \times 10^6$ CFU/mL | $4.3 \times 10^4$ CFU/mL |
| Control | $2.1 \times 10^8$ CFU/mL | $2.5 \times 10^8$ CFU/mL |

Synergy Calculation:
After 24 hours of contact, a 3 log $_{10}$ or greater reduction was achieved with:
PAA = >200 ppm (400 ppm)
TCMTB = >400 ppm (800 ppm)
PAA = 80 ppm/TCMTB = 200 ppm
SI = 80/400 + 200/800 = 0.45

EXAMPLE 3

When a blend of peroxyoctanoic acid and peracetic acid (POAA) was tested with 1-(3-chloroallyl)-3,5,7-triaza-1-azoniaadamantane chloride (D-75) in papermill process water at pH 7.0, the following synergistic activity was demonstrated.

| Biocide (ppm of product) | 5 Hour Contact | 24 Hour Contact |
|---|---|---|
| POAA @ 12.5 ppm | $4.3 \times 10^6$ CFU/mL | $1.1 \times 10^7$ CFU/mL |
| POAA @ 25 ppm | $5.9 \times 10^4$ CFU/mL | $6.1 \times 10^6$ CFU/mL |
| POAA @ 50 ppm | $<10^3$ CFU/mL | $2.6 \times 10^6$ CFU/mL |
| POAA @ 100 ppm | $<10^3$ CFU/mL | $<10^3$ CFU/mL |
| D-75 @ 50 ppm | $5.2 \times 10^6$ CFU/mL | $3.8 \times 10^5$ CFU/mL |
| D-75 @ 100 ppm | $3.2 \times 10^5$ CFU/mL | $1.0 \times 10^4$ CFU/mL |
| D-75 @ 200 ppm | $3.1 \times 10^4$ CFU/mL | $<10^3$ CFU/mL |
| D-75 @ 400 ppm | $7.0 \times 10^3$ CFU/mL | $<10^3$ CFU/mL |
| POA @ 20 ppm plus D-75 @ 50 ppm | $2.6 \times 10^4$ CFU/mL | $<10^3$ CFU/mL |
| D-75 @ 100 ppm | $<10^3$ CFU/mL | $<10^3$ CFU/mL |
| D-75 @ 200 ppm | $<10^3$ CFU/mL | $<10^3$ CFU/mL |
| Control | $7.2 \times 10^6$ CFU/mL | $1.8 \times 10^7$ CFU/mL |

Synergy Calculation:
After 5 hours of contact, a 3 log $_{10}$ of greater reduction was achieved with:
POAA = 50 ppm
D-75 = 400 ppm
POAA = 20 ppm/D75 = 100 ppm
SI = 20/50 + 100/400 = 0.65
After 24 hours of contact, a 3 log $_{10}$ or greater reduction was achieved with:
POAA = 100 ppm
D-75 = 200 ppm
POAA = 20 ppm/D75 = 50 ppm
SI = 20/100 + 50/200 = 0.45

EXAMPLE 4

Along with showing synergistic activity against bacteria, the peroctanoic acid described in example #22 is also synergistic against fungi. When *Aspergillus niger* spores were seeded into papermill whitewater, pH 7.0, and treated with a combination of POAA and 5-chloro-2-methyl-4-isothiazolin-3-one and 2-methyl-4-isothiazolin-3-one (Iso), the following synergistic activity was seen.

| Biocide (ppm of product) | 24 Hour Contact | 72 Hour Contact |
|---|---|---|
| POAA @ 100 ppm | $2.9 \times 10^4$ CFU/mL | $3.1 \times 10^4$ CFU/mL |
| POAA @ 250 ppm | $3.1 \times 10^3$ CFU/mL | $1.1 \times 10^3$ CFU/mL |
| POAA @ 500 ppm | $1.2 \times 10^1$ CFU/mL | $2.0 \times 10^0$ CFU/mL |
| Iso @ 25 ppm | $2.0 \times 10^4$ CFU/mL | $2.5 \times 10^4$ CFU/mL |
| Iso @ 50 ppm | $2.3 \times 10^4$ CFU/mL | $2.4 \times 10^4$ CFU/mL |
| Iso @ 100 ppm | $1.0 \times 10^4$ CFU/mL | $1.6 \times 10^4$ CFU/mL |
| Iso @ 200 ppm | $4.0 \times 10^3$ CFU/mL | $6.0 \times 10^3$ CFU/mL |
| POAA @ 250 ppm plus Iso @ 25 ppm | $6.1 \times 10^2$ CFU/mL | $1.5 \times 10^2$ CFU/mL |
| Iso @ 50 ppm | $5.0 \times 10^2$ CFU/mL | $1.5 \times 10^2$ CFU/mL |
| Iso @ 100 ppm | $4.6 \times 10^2$ CFU/mL | $1.0 \times 10^2$ CFU/mL |
| Iso @ 200 ppm | $3.6 \times 10^2$ CFU/mL | $1.1 \times 10^2$ CFU/mL |

| Biocide (ppm of product) | 24 Hour Contact | 72 Hour Contact |
|---|---|---|
| Control | $3.8 \times 10^4$ CFU/mL | $2.6 \times 10^4$ CFU/mL |

Synergy Calculation
After 24 hours of contact, a 2 log $_{10}$ reduction in fungal spores was achieved with:
POAA = 500 ppm
Iso = >200 ppm (400 ppm)
POAA = 250 ppm/Iso = 25 ppm
SI = 250/500 + 25/400 = 0.5625
After 24 hours of contact, a 2 log $_{10}$ or greater reduction was achieved with:
POAA = 500 ppm
Iso = >200 ppm (400 ppm)
POAA = 250 ppm/Iso = 25 ppm
SI = 250/500 + 25/400 = 0.5625

EXAMPLE 5

Another example of the synergy seen with the blend of peracetic acid and the peroctanoic acid is illustrated when POAA is applied to a papermill process water, pH 7.0, that has also been dosed with 4,5-dichloro-2-N-octyl-4-isothiazolin-3-one (RH287).

| Biocide (ppm of product) | 5 Hour Contact | 24 Hour Contact |
|---|---|---|
| POAA @ 25 ppm | $9.1 \times 10^6$ CFU/mL | $1.9 \times 10^7$ CFU/mL |
| POAA @ 50 ppm | $1.6 \times 10^5$ CFU/mL | $2.3 \times 10^7$ CFU/mL |
| POAA @ 100 ppm | $1 \times 10^3$ CFU/mL | $6.1 \times 10^5$ CFU/mL |
| POAA @ 200 ppm | $<10^3$ CFU/mL | $3.8 \times 10^4$ CFU/mL |
| RH287 @ 50 ppm | $2.1 \times 10^6$ CFU/mL | $7.1 \times 10^6$ CFU/mL |
| RH287 @ 100 ppm | $1.3 \times 10^5$ CFU/mL | $2.8 \times 10^6$ CFU/mL |
| RH287 @ 200 ppm | $1.6 \times 10^4$ CFU/mL | $1.1 \times 10^6$ CFU/mL |
| POAA @ 20 ppm plus RH287 @ 50 ppm | $1.1 \times 10^5$ CFU/mL | $5.6 \times 10^6$ CFU/mL |
| RH287 @ 100 ppm | $3.6 \times 10^4$ CFU/mL | $8.0 \times 10^4$ CFU/mL |
| RH287 @ 200 PPM | $8.0 \times 10^3$ CFU/mL | $6.0 \times 10^3$ CFU/mL |
| POAA @ 40 ppm plus RH287 @ 50 ppm | $8.0 \times 10^3$ CFU/mL | $2.7 \times 10^4$ CFU/mL |
| RH287 @ 100 ppm | $4.0 \times 10^3$ CFU/mL | $<10^3$ CFU/mL |
| RH287 @ 200 PPM | $3.0 \times 10^3$ CFU/mL | $<10^3$ CFU/mL |
| Control | $3.0 \times 10^7$ CFU/mL | $4.9 \times 10^7$ CFU/mL |

Synergy Calculation:
After 5 hours of contact, a 4 log $_{10}$ or greater reduction was achieved with:
POAA = 100 ppm
RH287 = >200 (400 ppm)
POAA = 40 ppm/RH287 = 50 ppm
SI = 40/100 + 50/400 = 0.525
After 24 hours of contact, a 4 log $_{10}$ or greater reduction was achieved with:
POAA = >200 ppm (400 ppm)
RH287 = >200 ppm (400 ppm)
POAA = 40 ppm/RH287 = 100 ppm
SI = 40/100 + 100/400 = 0.35

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims:

We claim:

1. A composition for inhibiting the growth of microorganisms comprising effective amounts of peracetic acid and a non-oxidizing biocide selected from the group consisting of 2-methyl-4,5-trimethylene-4-isothiazolin-3-one and 2-(thiocyanomethylthio)benzothiazole.

2. The composition of claim 1 wherein the amount of peracetic acid ranges from approximately 5 to 250 ppm and the amount of non-oxidizing biocide ranges from approximately 10 to 250 ppm.

3. A method for controlling the growth of microorganisms in industrial process water comprising the step of administering a sufficient amount of a peracetic acid and a sufficient amount of a non-oxidizing biocide selected from the group consisting of 2-methyl-4,5-trimethylene-4-isothiazolin-3-one and 2-(thiocyanomethylthio)benzothiazole to the industrial process water to inhibit the growth of the microorganisms.

4. The method of claim 3 wherein the industrial process water is selected from the group consisting of water of a pulp and paper mill system, cooling water and mining.

5. The method of claim 3 wherein the peracetic acid and the non-oxidizing biocide are added in a ratio from about 10:1 to 1:25.

6. The method of claim 3 wherein the amount of peracetic acid added ranges from approximately 5 to 250 ppm and the non-oxidizing biocide ranges from approximately 10 to 250 ppm.

7. The method of claim 3 wherein the microorganisms contain bacteria.

8. The method of claim 3 wherein the microorganisms contain fungi.

9. The method of claim 3 wherein the peracetic acid is added to the industrial water prior to the addition of the non-oxidizing biocide.

* * * * *